United States Patent [19]

Wüst et al.

[11] Patent Number: 4,801,707

[45] Date of Patent: Jan. 31, 1989

[54] PROCESS FOR THE PRODUCTION OF BENZOTHIAZOLE SULPHENE AMIDES

[75] Inventors: Alfredo Wüst, Roesrath, Fed. Rep. of Germany; Tony Van Osselaer, Belsele, Belgium

[73] Assignee: Bayer Aktiengesellschaft, Leverkusen, Fed. Rep. of Germany

[21] Appl. No.: 946,695

[22] Filed: Dec. 24, 1986

Related U.S. Application Data

[63] Continuation of Ser. No. 763,449, Aug. 7, 1985, abandoned.

[30] Foreign Application Priority Data

Aug. 18, 1984 [DE]  Fed. Rep. of Germany ....... 3430435

[51] Int. Cl.$^4$ .................. C07D 277/80; C07D 413/12
[52] U.S. Cl. .................................. 544/135; 544/368; 546/198; 548/167; 548/168
[58] Field of Search ................ 548/167, 168; 544/135, 544/368; 546/198

[56] References Cited

U.S. PATENT DOCUMENTS 4,127,454  12/1978  Torii et al. ................. 204/59 R
4,182,873   1/1980  Janin ........................ 544/133

FOREIGN PATENT DOCUMENTS 2744423  4/1978  Fed. Rep. of Germany .
2356686  5/1984  Fed. Rep. of Germany .

OTHER PUBLICATIONS

Isv. Vyssh. Uchebn. Zaved., Khimiya i khim. tekhnol., 22 (1979), 9, 1067–1070.

*Primary Examiner*—Mary E. Ceperley
*Attorney, Agent, or Firm*—Connolly and Hutz

[57] ABSTRACT

Benzothiazole sulphene amides are obtained from dibenzothiazolyl disulphide and water-soluble amines in the absence of an oxidizing agent and in the presence of aqueous alkali in a high yield and with very good stability in storage by placing the amine solution in water and simultaneously adding dibenzothiazolyl disulphide and aqueous alkali from separate storage vessels.

5 Claims, No Drawings

PROCESS FOR THE PRODUCTION OF BENZOTHIAZOLE SULPHENE AMIDES

This is a continuation of application Ser. No. 763,449 filed Aug. 7, 1985, abandoned.

This invention relates to a process for the production of benzothiazole sulphene amides from dibenzothiazolyl disulphides and water-soluble amines.

Benzothiazole sulphene amides are usually produced by oxidative coupling of 2-mercaptobenzothiazoles, or the alkali salts or disulphides thereof, and primary or secondary amines (DE-OS Nos. 2 356 686 and 2 744 423). In this process, either it is only possible to obtain moderate yields based on the mercaptobenzothiazole and the products are contaminated by by-products which impair the stability of the sulphene amide in storage, or complex and uneconomical processes with complicated purifying stages have to be adopted.

Yields of at most 90%, based on the amine, are obtained by the known processes. This is a substantial drawback as amines which are at least as expensive to produce as the mercaptobenzothiazole portion are used for the known sulphene amides which are known to be used as vulcanisation accelerators.

It is also known from Izv. vyssh. Uchebn. Zaved., Khimiya i khim. tekhnol., 22 (1979), 9, 1067–1070 that dibenzothiazolyl disulphide (MBTS) can be reacted with amines in the presence and absence of alkali and in the absence of an oxidizing agent.

Without alkali, a yield of 86% based on the starting mixture was obtained with morpholine as amine, and this only amounts to 50% because one mol of morpholine salt of mercaptobenzothiazole, which still has to be worked up with caustic soda solution in a separate operation, is formed for each mol of sulphene amide produced.

If caustic soda solution is added to produce the sodium salt of mercaptobenzothiazole (NaMBT) as reusable by-product and to reduce the quantity of amine to be used, the yield of sulphene amide falls to 10% as a function of the quantity of caustic soda solution.

An object of the invention is to provide an economical process for the production of purer benzothiazole sulphene amides in an improved yield and with improved stability in storage.

It has now surprisingly been found that the reaction of MBTS with water-soluble amines in the absence of oxidizing agents and in the presence of aqueous alkali can be successufily accomplished in a high yield to form pure and stable benzothiazole sulphene amides if certain conditions are observed when carrying out the reaction.

The invention therefore relates to a process for the production of benzothiazole sulphene amides from dibenzothiazolyl disulphide and a water-soluble amine in the absence of an oxidizing agent and in the presence of aqueous alkali, characterised in that the amine or a solution of the amine is placed in water and dibenzothiazolyl disulphide and aqueous alkali are added simultaneously from separate storage vessels.

The ratio of water to amine is preferably at most 20:1, in particular, at most 10:1 parts by weight.

The aqueous alkali is preferably added in such a way that the pH is adjusted to a value of from 10 to 13, more preferably from 11 to 12. The reaction is preferably carried out at a temperature of from 0° to 80° C., more preferably from 20° to 60° C.

The sulphene amide formed is separated. Excess amine is recovered from the mother liquor (by distillation) and mercaptobenzothiazole is recovered from the mother liquor (by precipitation with acid).

Caustic soda solution and caustic potash solution are particularly suitable as aqueous alkali.

All amines which are soluble to at least 1% by weight with a $pK_s < 7$ (in aqueous solution) can be used as amines, in particular methyl amine, ethyle amine, dimethyl amine, diethyl amine, n-propyl amine, isopropyl amine, butyl amines, pentyl amines, cyclopentyl amine, cyclohexyl amine, piperazine, morpholine, pyrrolidine and piperidine.

The process according to the invention is particularly valuable when using cyclohexyl amine, tertiary butyl amine, isopropyl amine and morpholine.

EXAMPLE 1

N-Cyclohexyl-2-benzothiazole sulphene amide 100 g of cyclohexyl amine and 300 g of water were placed in a 2 litre multiple neck flask with stirrer, dropping funnel, cooler, thermometer and pH electrode ad were heated to 50° C. 166 g of dibenzothiazolyl disulphide were introduced in small batches within a period of from 10 to 15 minutes. At the same time, 40 g of 50% by weight caustic soda solution were added dropwise so that the pH was between 11 and 12. Once addition was completed, stirring was continued for up to 2 hours, the precipitate was suction-filtered, washed with water and dried in a vacuum drying cabinet at 60° C. The cyclohexyl amine was recovered from the mother liquor and washing water by distillation. The mercaptobenzothiazole from the distillation sump was precipitated by addition of 25% sulphuric acid, was suction-filtered, washed with water and dried at 60° C. in a vacuum drying cabinet.

Yield from 96 to 97% of theoretical yield; content from 97 to 98%; amine content 0.2%; insoluble in ethanol 0%. Cyclohexyl amine recovery: 97%, mercaptobenzothiazole recovery 100%.

After ageing from 24 hours at 60° C. in a water-moist atmosphere: content 96.7%, amine content 0.4%, insoluble in ethanol 0%.

EXAMPLE 2

N-tert-butyl-2-benzothiazole sulphene amide 219 g of t-butyl amine were placed in an apparatus according to Example 1. 166 g of dibenzothiazolyl disulphide were introduced in small portions within a period of from 10 to 15 minutes with stirring at room temperature (from 20° to 30° C.). At the same time, a total of 240 g of 8.3% by weight caustic soda solution were added so that a pH of at least 11 was maintained. The mixture was stirred for a further 2 hours, the precipitate was suction-filtered, washed with water and dried in a vacuum drying cabinet at 60° C.

Yield 96% based on dibenzothiazolyl disulphide, 95.5% based on t-butyl amine. Content 98.4%, amine content 0.3%, insoluble in ethanol 0%, melting point 109° to 111° C.

After ageing for 24 hours at 60° C. in water-moist atmosphere: content 98.2%, amine content 0.3%, insoluble in ethanol 0%.

EXAMPLE 3

4-(2-benzothiazolylthio)-morpholin 261 g of morpholine were placed in an apparatus according to Example 1. 166 g of dibenzothiazolyl disulphide were added to room temperature within 20 minutes with stirring and 240 g of 8.3% by weight caustic soda solution were added at the same time.

After stirring for a further 2 hours, the solid material was suction-filtered, washed with water and dried in a vacuum cabinet at 50° C.

Yield 96.5% based on dibenzolthiazolyl disulphide, 94% on morpholine. Content 98%, amine content 0.2%, insoluble in ethanol 0%, melting point 84° to 86° C.

EXAMPLE 4

N-isopropyl-2-benzothiazole sulphene amide 236 g of isopropyl amine and 100 g of water were placed in an apparatus according to Example 1. 166 g of dibenzolthiazolyl disulphide were added within 20 minutes with stirring at from 20° to 30° C. and 80 g of 25% by weight caustic soda solution were added at the same time. On completion of the reaction, the mixture was stirred for a further 2 hours and the precipitate was suction-filtered, then washed with water and dried in a vacuum drying cabinet at 60° C.

Yield 97.5% based on dibenzothiazolyl disulphide, 95% based on isopropyl amine. Content 97.7%, amine content 0.2%, insoluble in ethanol 0%, melting point 94° to 96° C.

After ageing (see Example 1) content 96.2%, amine content 0.3%, melting point 93° to 96° C.

EXAMPLE 5

N-tert-butyl-2-benzothiazole sulphene amide 219 g of t-butyl amine were placed in an apparatus according to Example 1, also equipped with a feed screw and an overflow. 166 g of dibenzothiazolyl disulphide were introduced at room temperature (from 20° to 30° C.) in small batches within a period of from 10 to 15 minutes with stirring. At the same time, a total of 240 g of 8.3% by weight caustic soda solution were added so that a pH of at least 11 was maintained. 332 g of dibenzothiazolyl disulphide, 438 g of t-butyl amine and 480 g of 8.3 % by weight caustic soda solution were added hourly with stirring at from 20° to 30° C. The reaction mixture was removed continuously via the overflow and separated into solid matter and mother liquor by filtration. N-tert-butyl-benzothiazole sulphene amide is obtained after washing and drying as in Example 2.

Content 98.5%, amine content 0.15%, insoluble in ethanol 0%, melting point 107 to 110° C.; after ageing: content 98.1% amine content 0.16%, insoluble in ethanol 0%.

We claim:

1. A process for the production of benzothiazole sulphene amides from dibenzothiazolyl disulphide and a water-soluble amine in the absence of an oxidizing agent and in the presence of aqueous alkali, characterised in that the amine or an aqueous solution of the amine is placed in water and dibenzothiazolyl disulphide and aqueous alkali are added simultaneously from separate storage vessels such that the resulting mixture pH is adjusted to a value of from 10 to 13 by the added aqueous alkali.

2. A process according to claim 1, characterised in that tert-butyl amine, cyclohexyl amine, isopropyl amine or morpholine are added as the amine.

3. A process according to claim 1, characterized in that aqueous alkali is added in such a way that the pH is adjusted to a value of from 11 to 12.

4. A process according to claim 1 characterized in that the reaction is carried out at from 0° to 80° C.

5. A process according to claim 1, characterized in that the reaction is carried out at from 20° to 60° C.

* * * * *

PROCESS FOR THE PRODUCTION OF BENZOTHIAZOLE SULPHENE AMIDES

This is a continuation of application Ser. No. 763,449 filed Aug. 7, 1985, abandoned.

This invention relates to a process for the production of benzothiazole sulphene amides from dibenzothiazolyl disulphides and water-soluble amines.

Benzothiazole sulphene amides are usually produced by oxidative coupling of 2-mercaptobenzothiazoles, or the alkali salts or disulphides thereof, and primary or secondary amines (DE-OS Nos. 2 356 686 and 2 744 423). In this process, either it is only possible to obtain moderate yields based on the mercaptobenzothiazole and the products are contaminated by by-products which impair the stability of the sulphene amide in storage, or complex and uneconomical processes with complicated purifying stages have to be adopted.

Yields of at most 90%, based on the amine, are obtained by the known processes. This is a substantial drawback as amines which are at least as expensive to produce as the mercaptobenzothiazole portion are used for the known sulphene amides which are known to be used as vulcanisation accelerators.

It is also known from Izv. vyssh. Uchebn. Zaved., Khimiya i khim. tekhnol., 22 (1979), 9, 1067–1070 that dibenzothiazolyl disulphide (MBTS) can be reacted with amines in the presence and absence of alkali and in the absence of an oxidizing agent.

Without alkali, a yield of 86% based on the starting mixture was obtained with morpholine as amine, and this only amounts to 50% because one mol of morpholine salt of mercaptobenzothiazole, which still has to be worked up with caustic soda solution in a separate operation, is formed for each mol of sulphene amide produced.

If caustic soda solution is added to produce the sodium salt of mercaptobenzothiazole (NaMBT) as reusable by-product and to reduce the quantity of amine to be used, the yield of sulphene amide falls to 10% as a function of the quantity of caustic soda solution.

An object of the invention is to provide an economical process for the production of purer benzothiazole sulphene amides in an improved yield and with improved stability in storage.

It has now surprisingly been found that the reaction of MBTS with water-soluble amines in the absence of oxidizing agents and in the presence of aqueous alkali can be successuflly accomplished in a high yield to form pure and stable benzothiazole sulphene amides if certain conditions are observed when carrying out the reaction.

The invention therefore relates to a process for the production of benzothiazole sulphene amides from dibenzothiazolyl disulphide and a water-soluble amine in the absence of an oxidizing agent and in the presence of aqueous alkali, characterised in that the amine or a solution of the amine is placed in water and dibenzothiazolyl disulphide and aqueous alkali are added simultaneously from separate storage vessels.

The ratio of water to amine is preferably at most 20:1, in particular, at most 10:1 parts by weight.

The aqueous alkali is preferably added in such a way that the pH is adjusted to a value of from 10 to 13, more preferably from 11 to 12. The reaction is preferably carried out at a temperature of from 0° to 80° C., more preferably from 20° to 60° C.

The sulphene amide formed is separated. Excess amine is recovered from the mother liquor (by distillation) and mercaptobenzothiazole is recovered from the mother liquor (by precipitation with acid).

Caustic soda solution and caustic potash solution are particularly suitable as aqueous alkali.

All amines which are soluble to at least 1% by weight with a $pK_s<7$ (in aqueous solution) can be used as amines, in particular methyl amine, ethyle amine, dimethyl amine, diethyl amine, n-propyl amine, isopropyl amine, butyl amines, pentyl amines, cyclopentyl amine, cyclohexyl amine, piperazine, morpholine, pyrrolidine and piperidine.

The process according to the invention is particularly valuable when using cyclohexyl amine, tertiary butyl amine, isopropyl amine and morpholine.

EXAMPLE 1

N-Cyclohexyl-2-benzothiazole sulphene amide 100 g of cyclohexyl amine and 300 g of water were placed in a 2 litre multiple neck flask with stirrer, dropping funnel, cooler, thermometer and pH electrode ad were heated to 50° C. 166 g of dibenzothiazolyl disulphide were introduced in small batches within a period of from 10 to 15 minutes. At the same time, 40 g of 50% by weight caustic soda solution were added dropwise so that the pH was between 11 and 12. Once addition was completed, stirring was continued for up to 2 hours, the precipitate was suction-filtered, washed with water and dried in a vacuum drying cabinet at 60° C. The cyclohexyl amine was recovered from the mother liquor and washing water by distillation. The mercaptobenzothiazole from the distillation sump was precipitated by addition of 25% sulphuric acid, was suction-filtered, washed with water and dried at 60° C. in a vacuum drying cabinet.

Yield from 96 to 97% of theoretical yield; content from 97 to 98%; amine content 0.2%; insoluble in ethanol 0%. Cyclohexyl amine recovery: 97%, mercaptobenzothiazole recovery 100%.

After ageing from 24 hours at 60° C. in a water-moist atmosphere: content 96.7%, amine content 0.4%, insoluble in ethanol 0%.

EXAMPLE 2

N-tert-butyl-2-benzothiazole sulphene amide 219 g of t-butyl amine were placed in an apparatus according to Example 1. 166 g of dibenzothiazolyl disulphide were introduced in small portions within a period of from 10 to 15 minutes with stirring at room temperature (from 20° to 30° C.). At the same time, a total of 240 g of 8.3% by weight caustic soda solution were added so that a pH of at least 11 was maintained. The mixture was stirred for a further 2 hours, the precipitate was suction-filtered, washed with water and dried in a vacuum drying cabinet at 60° C.

Yield 96% based on dibenzothiazolyl disulphide, 95.5% based on t-butyl amine. Content 98.4%, amine content 0.3%, insoluble in ethanol 0%, melting point 109° to 111° C.

After ageing for 24 hours at 60° C. in water-moist atmosphere: content 98.2%, amine content 0.3%, insoluble in ethanol 0%.

EXAMPLE 3

4-(2-benzothiazolylthio)-morpholin 261 g of morpholine were placed in an apparatus according to Example 1. 166 g of dibenzothiazolyl disulphide were added to room temperature within 20 minutes with stirring and 240 g of 8.3% by weight caustic soda solution were added at the same time.

After stirring for a further 2 hours, the solid material was suction-filtered, washed with water and dried in a vacuum cabinet at 50° C.

Yield 96.5% based on dibenzolthiazolyl disulphide, 94% on morpholine. Content 98%, amine content 0.2%, insoluble in ethanol 0%, melting point 84° to 86° C.

EXAMPLE 4

N-isopropyl-2-benzothiazole sulphene amide 236 g of isopropyl amine and 100 g of water were placed in an apparatus according to Example 1. 166 g of dibenzolthiazolyl disulphide were added within 20 minutes with stirring at from 20° to 30° C. and 80 g of 25% by weight caustic soda solution were added at the same time. On completion of the reaction, the mixture was stirred for a further 2 hours and the precipitate was suction-filtered, then washed with water and dried in a vacuum drying cabinet at 60° C.

Yield 97.5% based on dibenzothiazolyl disulphide, 95% based on isopropyl amine. Content 97.7%, amine content 0.2%, insoluble in ethanol 0%, melting point 94° to 96° C.

After ageing (see Example 1) content 96.2%, amine content 0.3%, melting point 93° to 96° C.

EXAMPLE 5

N-tert-butyl-2-benzothiazole sulphene amide 219 g of t-butyl amine were placed in an apparatus according to Example 1, also equipped with a feed screw and an overflow. 166 g of dibenzothiazolyl disulphide were introduced at room temperature (from 20° to 30° C.) in small batches within a period of from 10 to 15 minutes with stirring. At the same time, a total of 240 g of 8.3% by weight caustic soda solution were added so that a pH of at least 11 was maintained. 332 g of dibenzothiazolyl disulphide, 438 g of t-butyl amine and 480 g of 8.3 % by weight caustic soda solution were added hourly with stirring at from 20° to 30° C. The reaction mixture was removed continuously via the overflow and separated into solid matter and mother liquor by filtration. N-tert-butyl-benzothiazole sulphene amide is obtained after washing and drying as in Example 2.

Content 98.5%, amine content 0.15%, insoluble in ethanol 0%, melting point 107 to 110° C.; after ageing: content 98.1% amine content 0.16%, insoluble in ethanol 0%.

We claim:

1. A process for the production of benzothiazole sulphene amides from dibenzothiazolyl disulphide and a water-soluble amine in the absence of an oxidizing agent and in the presence of aqueous alkali, characterised in that the amine or an aqueous solution of the amine is placed in water and dibenzothiazolyl disulphide and aqueous alkali are added simultaneously from separate storage vessels such that the resulting mixture pH is adjusted to a value of from 10 to 13 by the added aqueous alkali.

2. A process according to claim 1, characterised in that tert-butyl amine, cyclohexyl amine, isopropyl amine or morpholine are added as the amine.

3. A process according to claim 1, characterized in that aqueous alkali is added in such a way that the pH is adjusted to a value of from 11 to 12.

4. A process according to claim 1 characterized in that the reaction is carried out at from 0° to 80° C.

5. A process according to claim 1, characterized in that the reaction is carried out at from 20° to 60° C.

* * * * *